(12) United States Patent
Lee

(10) Patent No.: US 11,571,382 B1
(45) Date of Patent: Feb. 7, 2023

(54) HERBAL SHAMPOO COMPOSITION AND METHOD FOR PREPARING THE SAME

(71) Applicant: Saeang Co., Ltd., Namyangju-si (KR)

(72) Inventor: Dongkyu Lee, Namyangju-si (KR)

(73) Assignee: SAEANG CO., LTD., Namyangju-Si (KR)

( * ) Notice: Subject to any disclaimer, the term of this patent is extended or adjusted under 35 U.S.C. 154(b) by 0 days.

(21) Appl. No.: 17/816,008

(22) Filed: Jul. 29, 2022

(30) Foreign Application Priority Data

Aug. 2, 2021 (KR) .......................... 10-2021-0101282

(51) Int. Cl.
| | | |
|---|---|---|
| *A01N 35/06* | (2006.01) | |
| *A61K 8/9789* | (2017.01) | |
| *A61Q 5/02* | (2006.01) | |
| *A61K 8/9794* | (2017.01) | |
| *A61Q 7/00* | (2006.01) | |

(52) U.S. Cl.
CPC .......... *A61K 8/9789* (2017.08); *A61K 8/9794* (2017.08); *A61Q 5/02* (2013.01); *A61Q 7/00* (2013.01); *A61K 2800/591* (2013.01); *A61K 2800/805* (2013.01)

(58) Field of Classification Search
None
See application file for complete search history.

(56) References Cited

U.S. PATENT DOCUMENTS 7,648,717 B2 * 1/2010 Lo .................... A61K 36/638
424/725

FOREIGN PATENT DOCUMENTS

| KR | 10-2000-0031349 A | 6/2000 |
|---|---|---|
| KR | 10-0982414 B1 | 9/2010 |
| KR | 10-1017709 B1 | 2/2011 |
| KR | 10-2012-0038585 A | 4/2012 |
| KR | 10-1358895 B1 | 2/2014 |
| KR | 10-2014-0111903 A | 9/2014 |
| KR | 10-1451337 B1 | 10/2014 |
| KR | 10-1953779 B1 | 3/2019 |
| KR | 10-2296279 B1 | 9/2021 |
| KR | 10-2002-0076834 A | 10/2022 |

OTHER PUBLICATIONS

Good Shampoo for Hair Loss Manage scalp fever with Lee Moonwon Shampoo, Sep. 13, 2020, https//blog.naver.com/jiyeon4847/222088303478.
Nature republic Black Bean Shampoo should be caught in the hair loss field, Mar. 22, 2021, https://blog.naver.com/ysook6587/222283825844.
Notamo Hair Tonic Review scalp care with hair cooling, Apr. 6, 2021, https://blog.naver.com/nanryangb/222300025224.

* cited by examiner

*Primary Examiner* — Dominic Lazaro
(74) *Attorney, Agent, or Firm* — KORUS Patent, LLC; Seong Il Jeong

(57) ABSTRACT

An oriental shampoo composition that can help maintain the health of the scalp and hair and help alleviate hair loss is provided. The shampoo composition includes, among others, 47.89% by weight of purified water; 10.00% by weight of a herbal mixed solution containing purified water, Rehmannia chinensis root extract, butylene glycol, Mentha arvensis extract, 1,2-hexanediol, Acorus gramineus root extract, Biota orientalis leaf extract, Chrysanthemum zawadskii extract, Panax ginseng root extract, Glycyrrhiza galbra (licorice) root extract, Lycinum chinense fruit extract, Morus alba bark extract, Xanthium strumarium fruit extract, and ethyl hexyl glycerin; 10.00% by weight of a mixed solution containing sodium lauryl sulfate, purified water, disodium phosphate and sodium carbonate; 10.00% by weight of a mixed solution containing purified water, TEA-lauryl sulfate and sodium benzoate; and 8.0% by weight of a mixed solution containing purified water, cocamidopropyl betaine and sodium chloride.

2 Claims, 1 Drawing Sheet

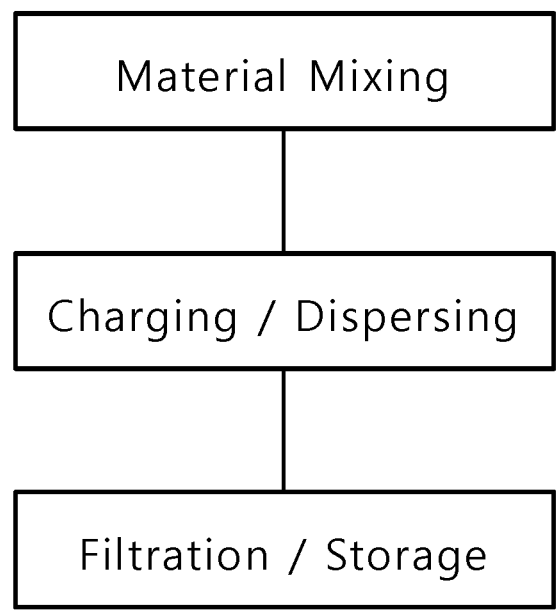

HERBAL SHAMPOO COMPOSITION AND METHOD FOR PREPARING THE SAME

CROSS-REFERENCE TO RELATED APPLICATION(S)

This application claims the benefit of Korean Patent Application No. 10-2021-0101282 filed on Aug. 2, 2021 with the Korean Intellectual Property Office, the entire content of which is incorporated herein by reference.

The present invention relates to an oriental herbal shampoo composition and a method for preparing the same, and more particularly, an oriental herbal shampoo composition that not only maintains the health of the scalp and hair by applying intensive oriental herbal extracts in a complex manner, but also can neutralize alkalized hair with a weak acidity to make damaged hair healthy and can help alleviate hair loss, and a method for preparing the same.

Background

Generally, it is known that the number of hairs in the human body is about 100,000 to 150,000, and the hairs are formed by hair follicles. The hair follicle has a nipple, and small blood vessels are distributed in this area to supply the nutrients necessary for hair growth.

It has been reported that each hair has a different cycle and grows and falls out through a growth phase, a catagen phase, and a telogen phase. These cycles are repeated over 3 to 6 years, and it is known that an average of about 50 to 100 hairs are lost each day. In general, alopecia refers to a decrease in the proportion of hair in the growing phase, an increase in the number of hairs in the catagen or telogen phase, and thus an abnormally large number of hairs falling out in these cycles.

As the cause of such hair loss, the theory of excessive male hormone action, the theory of excessive sebum secretion, the theory of poor blood circulation, the theory of scalp dysfunction due to peroxides and bacteria, genetic factors, aging, stress and the like are being discussed. In general, it has been reported that testosterone, which is a type of male hormone, is enzymatically activated into dehydrotestosterone (DHT), this DHT binds to a specific receptor and induces a protein that causes hair loss to cause hair loss. Further, such a mechanism may cause excessive production of sebum, which may cause acne, seborrheic dermatitis, and the like, resulting in hair loss accompanied by inflammation on the scalp.

For modern people, it is considered that stress, meat-oriented eating habits, irregular lifestyle, and use of products containing chemical ingredients such as shampoo and hair products are the main factors for hair loss rather than genetic factors. Currently, the hair loss population is increasing, regardless of men and women, in their 50s and 60s, as well as office workers in their 30s and university students in their 20s.

Various anti-hair loss agents and hair growth promoters have been developed to enable active hair growth in the pores of the scalp while preventing the symptoms of empty hair due to the above hair loss phenomenon.

In general, formulations widely used for the treatment and prevention of alopecia include formulations containing minoxidil. Minoxidil was originally an antihypertensive drug developed to lower blood pressure, but while the hair growth phenomenon appears due to a side effect of use, today, it is a drug that has become more famous as a hair growth agent. However, minoxidil formulations have been found to be unsuitable for long-term use because they cause side effects such as scalp dryness and scalp irritation such as erythema, allergic contact dermatitis, hirsutism on the face and vasodilation, feeling of collapse due to antihypertensive action, hypotension, and tachycardia when used excessively.

In addition, various therapeutic agents have been proposed, but the therapeutic effect is effective at the time of administration, but when the use of the drug is stopped, there is a problem in that hair loss progresses again like non-users after several months. It is also difficult for general consumers to use because the price is too high, and there are also problems that side effects such as decreased libido and erectile dysfunction occur when taking it.

In recent years, in South Korea, a method of using natural herbal medicines or natural plant extracts for preventing hair loss and promoting hair growth has been tried. For example, Korean Unexamined Patent Publication No. 10-2000-0031349 discloses a hair growth composition using oriental herbal extracts such as ginseng, Cengon, false daisy, Psoraleae Semen, angelica (dong quai) and Biota Orientalis Leaf Folium, Korean Unexamined Patent Publication No. 10-2002-0076834 discloses a hair growth promoting composition and a method for preparing the same, using as main materials of bark of Euonymus tricocarpus (ogapi), Panax Ginseng Root and apple juice.

In addition, Korean Patent Registration No. 10-0982414 discloses a hair growth composition including Acdrus asiaticus extract, Coicis semen extract, flax seed oil and alpha-tocopherol, and Korean Unexamined Patent Publication No. 10-2012-0038585 discloses an oriental herbal extract for preventing hair loss, including a mixed extract of Coptis Chinensis, Phellodendri Cortex, Scutellariae Radix, Polygonati Rhizoma, Astragalus membranaceus, Angelica dahurica BENTHAM et Hooker, Chrysanthemum indicum L., Licorice and ginger.

Further, Korean Patent Registration No. 10-1451337 discloses A method for producing a composition for preventing hair loss and promoting hair growth using Biota Orientalis Leaf, Siegesbeckiae Herba leaves, liriope rhizome, Licorice, morus barks, Scutellariae Radix, Acorus Gramineuss, and the like.

As described above, most of the conventional anti-hair loss (and hair growth promotion) compositions includes oriental herbal extracts, such as ginseng, Cengon, bark of Euonymus tricocarpus, Coptis Chinensis and the like as main ingredients, which are known to be effective in preventing hair damage and hair loss, and the other natural ingredients are added.

Hair loss is often caused by a combination of not only the degeneration of the scalp cells due to aging, the lack of nutrients supplied to the hair roots, but also inflammation and pore clogging caused by fat or foreign materials or scalp disease. Also, in recent years, since hair loss caused by environmental and bacterial factors as well as genetic factors is increasing, it is important to keep the scalp clean.

However, the composition for preventing hair loss (and promoting hair growth) using a conventional oriental herbal extract does not show a sufficient effect in preventing hair loss (and promoting hair growth), and the like, or there is a problem that the efficacy is lowered compared to the amount used. Further, when using a conventional herbal medicine extract, there is a problem that the function of inhibiting bacteria on the scalp or maintaining a clean scalp is insignificant, and the consumer's preference is low due to the lack of freshness.

Prior Art Literature
Patent Literature
(Patent Literature 1) Korean Unexamined Patent Publication No. 10-2000-0031349
(Patent Literature 2) Korean Patent Registration No. 10-0982414

DETAILED DESCRIPTION OF THE INVENTION

Technical Problem

The present invention has been designed to solve the conventional problems as described above, and an object of the present invention is to provide an oriental herbal shampoo composition for hair loss prevention and scalp protection that can help maintain the health of the scalp and hair, as well as help alleviate hair loss, by applying intensive oriental herbal extracts in combination.

Another object of the present invention is to provide a method for preparing an oriental herbal shampoo composition that not only maintains the health of the scalp and hair by complex application of intensive oriental herbal extracts, but also neutralizes the alkalized hair with a weak acid to make damaged hair healthy.

Another object of the present invention is to provide an intensive oriental herbal shampoo composition containing herbal extracts that can help alleviate hair loss, relieve dandruff, and nourish the scalp.

Yet another object of the present invention is to provide an oriental herbal shampoo composition that manages healthy hair with abundant fine bubbles and clean scalp care, and provides nutrition to the scalp so that it can be managed as a healthy scalp.

A further object of the present invention is to provide an oriental herbal shampoo composition that contains a fermented liquid of natural medicinal extracts as an active ingredient, thus has excellent hair loss prevention and hair growth promotion functions, keeps hair and scalp clean, and has an improved refreshing feeling.

Technical Solution

In order to achieve the above objects, according to the present invention, there is provided a shampoo composition comprising: 47.89% by weight of purified water; 10.00% by weight of a herbal mixed solution containing purified water, Rehmannia Chinensis root extract, butylene glycol, Mentha Arvensis Extract, 1,2-hexanediol, Acorus Gramineus Root Extract, Biota Orientalis Leaf Extract, Chrysanthemum Zawadskii Extract, Panax Ginseng Root Extract, Glycyrrhiza Galbra (Licorice) Root Extract, Lycinum Chinense Fruit Extract, Morus Alba Bark Extract, Xanthium Strumarium Fruit Extract, and ethyl hexyl glycerin; 10.00% by weight of a mixed solution containing sodium lauryl sulfate, purified water, disodium phosphate and sodium carbonate; 10.00% by weight of a mixed solution containing purified water, TEA-lauryl sulfate and sodium benzoate; 8.0% by weight of a mixed solution containing purified water, cocamidopropyl betaine and sodium chloride; 3.0% by weight of a mixed solution containing purified water, disodium cocoamphodiacetate, sodium lauryl sulfate, hexylene glycol and sodium chloride; 2.8% by weight of a mixed solution containing purified water and acrylate copolymer; 2.5% by weight of Cocamide DEA; 2.0% by weight of Lauramide DEA; 1.0% by weight of dipropylene glycol; 1.0% by weight of a mixed solution containing purified water, amodimethicone, C12-14 Sec-Pareth-7, propylene glycol and phenoxy ethanol; 0.46% by weight of sodium benzoate; 0.3% by weight of Guar hydroxypropyltrimonium chloride; 0.3% by weight of caprylyl glycol; 0.2% by weight of salicylic acid; 0.2% by weight of Panthenol; 0.2% by weight of Panthenol; 0.1% by weight of a mixed solution containing Maltodextrin and Caramel; 0.1% by weight of Niacinamide; 0.1% by weight of sodium chloride; 0.04% by weight of fragrance; 0.0001% by weight of Cocos Nucifera (Coconut) oil; and 0.0001% by weight of citric acid.

Further, the herbal mixed solution is characterized by containing 1.6% by weight of Rehmannia Chinensis root extract; 0.5% by weight of butylene glycol; 0.4% by weight of Mentha Arvensis Extract; 0.3% by weight of 1,2-hexanediol; 0.1% by weight of Acorus Gramineus Root Extract; 0.1% by weight of Biota Orientalis Leaf Extract; 0.1% by weight of Chrysanthemum Zawadskii Extract; 0.1% by weight of Panax Ginseng Root Extract; 0.1% by weight of Glycyrrhiza Galbra (Licorice) Root Extract; 0.1% by weight of Lycinum Chinense Fruit Extract; 0.1% by weight of Morus Alba Bark Extract; 0.1% by weight of Xanthium Strumarium Fruit Extract; and 0.005% by weight of ethyl hexyl glycerin with respect to 10% by weight of the entire mixture.

Further, a method for preparing an oriental herbal shampoo composition according to the present invention includes the steps of:

a) charging a mixture of purified water, Rehmannia Chinensis root extract, butylene glycol, Mentha Arvensis Extract, 1,2-hexanediol, Acorus Gramineus Root Extract, Biota Orientalis Leaf Extract, Chrysanthemum Zawadskii Extract, Panax Ginseng Root Extract, Glycyrrhiza Galbra (Licorice) Root Extract, Lycinum Chinense Fruit Extract, Morus Alba Bark Extract, Xanthium Strumarium Fruit Extract, ethyl hexyl glycerin, sodium lauryl sulfate, disodium phosphate, sodium carbonate, dipropylene glycol, maltodextrin, Caramel in an oil phase dissolution tank, stirring and warming the mixture;

b) charging a mixture of purified water, TEA-lauryl sulfate, sodium benzoate, cocamidopropyl betaine, sodium chloride, disodium cocoamphodiacetate, sodium lauryl sulfate, hexylene glycol, Cocamide DEA, and Lauramide DEA in an emulsification tank, and stirring the mixture at room temperature;

c) charging salicylic acid in an emulsification tank, stirring and warming the mixture;

d) charging and dispersing a mixed solution of guar hydroxypropyltrimonium chloride in a separate dissolution tank;

e) charging a mixed solution of purified water and guar hydroxypropyltrimonium chloride in a separate dissolution tank, and then charging and stirring the mixed solution in an emulsification tank;

f) charging and dispersing a mixed solution of purified water and acrylate copolymer in a separate dissolution tank;

g) charging and stirring a mixed solution of purified water and acrylate copolymer in an emulsification tank and stirring the mixed solution;

h) charging and stirring a mixed solution of purified water, amodimethicone, C12-14 Sec-Pareth-7, propylene glycol, phenoxy ethanol, sodium benzoate, Dexpanthenol, Maltodextrin, Caramel, Niacinamide, sodium chloride, Cocos Nucifera (Coconut) oil, citric acid and fragrance in an emulsification tank; and i) checking the state of the emulsification tank, followed by filtration and storage.

In addition, the filtration may be carried out with a screen of 100 mesh.

Advantageous Effects

The present invention can provide an oriental herbal shampoo composition for hair loss prevention and scalp protection that can help maintain the health of the scalp and hair, as well as help alleviate hair loss, by applying intensive oriental herbal extracts in combination.

Also, the present invention can not only maintain the health of the scalp and hair by complex application of intensive oriental herbal extracts, but also neutralizes the alkalized hair with a weak acid to make damaged hair healthy.

Additionally, the present invention can provide an intensive oriental herbal shampoo composition containing herbal extracts that can help alleviate hair loss, relieve dandruff, and nourish the scalp.

Further, the present invention has the effect of managing healthy hair with abundant fine bubbles and clean scalp care, and providing nutrition to the scalp so that it can be managed as a healthy scalp.

Further, the present invention can provide an oriental herbal shampoo composition that contains a fermented liquid of natural medicinal extracts as an active ingredient, thus has excellent hair loss prevention and hair growth promotion functions, keeps hair and scalp clean, and has an improved refreshing feeling.

BRIEF DESCRIPTION OF THE DRAWINGS

FIGURE is an embodiment showing a preparation method according to the oriental herbal shampoo composition according to the present invention, and is a process flow chart showing a method for preparing an oriental herbal shampoo composition according to the present invention.

DETAILED DESCRIPTION OF THE EMBODIMENTS

While the present invention can be modified in various ways and take on various alternative forms, specific embodiments thereof are shown in the accompanying drawings and described in detail below. However, it should be understood that there is no intent to limit the present invention to the particular forms disclosed, but on the contrary, the present invention covers all modifications, equivalents, and alternatives falling within the spirit and scope of the present invention.

The present invention is not limited to the disclosed embodiments, but may be implemented in various different ways. The present embodiments are provided to only complete the disclosure of the present invention and to allow a person having ordinary skill in the art to completely understand the category of the invention.

Hereinafter, an embodiment of the present invention will be described in detail with reference to the attached drawings. Reference should now be made to the drawings, in which the same reference numerals are used throughout the different drawings to designate the same or similar components. However, in the following description, a detailed explanation of known related technologies may be omitted to avoid unnecessarily obscuring the subject matter of the present invention.

Figure is an embodiment showing a preparation method according to the oriental herbal shampoo composition according to the present invention.

An oriental herbal shampoo composition according to the present invention, and a method for preparing an oriental shampoo composition are provided.

As used herein, the "prevention of hair loss" includes not only substantial hair loss prevention, but also prevention of hair loss and/or promotion of hair growth (promotion of hair), and the like.

Therefore, the oriental herbal shampoo composition according to the present invention includes, as active ingredients for preventing hair loss, Rehmannia Chinensis root extract, Acorus Gramineus Root Extract, Biota Orientalis Leaf Extract, Chrysanthemum Zawadskii Extract, Panax Ginseng Root Extract, Glycyrrhiza Galbra (Licorice) Root Extract, Lycinum Chinense Fruit Extract, Morus Alba Bark Extract, and Xanthium Strumarium Fruit Extract.

According to the present invention, medicinal materials specified as natural materials are used, but they are contained as a fermentation broth, and have excellent hair loss prevention ability by activating the active ingredients contained in the medicinal materials and producing new active ingredients.

In the present invention, the type and/or formulation of the oriental herbal shampoo composition is not particularly limited. In the present invention, the composition for preventing hair loss is applied to the hair and/or scalp of the human body, and is included in the present invention regardless of its type or formulation.

The oriental herbal shampoo composition according to the present invention includes, in the type of the product form, products such as: hair cleaners for cleaning hair (shampoo, conditioner, soap, etc.); hair cosmetics for the beauty of hair; dyes for dyeing hair; a hair loss inhibitor that prevents hair loss; a hair growth promoter that promotes hair growth; and/or a scalp disease treatment/prevention agent for treating or preventing scalp disease.

A specific example of the oriental medicine composition according to the present invention may include one or more products selected from shampoo, rinse, soap, hair spray, hair gel, hair conditioner, scalp mask, dye, scalp therapeutic agent (atopic therapeutic agent, etc.), hair loss prevention agent, hair growth promoter, and the like. In addition, the hair loss prevention composition according to the present invention may be in a solid type, a liquid type, a spray type, an ointment type and/or a gel type in its formulation, but is not limited thereto.

The oriental herbal shampoo composition according to the present invention includes 47.89% by weight of purified water; 10.00% by weight of a herbal mixed solution containing purified water, Rehmannia Chinensis root extract, butylene glycol, Mentha Arvensis Extract, 1,2-hexanediol, Acorus Gramineus Root Extract, Biota Orientalis Leaf Extract, Chrysanthemum Zawadskii Extract, Panax Ginseng Root Extract, Glycyrrhiza Galbra (Licorice) Root Extract, Lycinum Chinense Fruit Extract, Morus Alba Bark Extract, Xanthium Strumarium Fruit Extract, and ethyl hexyl glycerin; 10.00% by weight of a mixed solution containing sodium lauryl sulfate, purified water, disodium phosphate and sodium carbonate; 10.00% by weight of a mixed solution containing purified water, TEA-lauryl sulfate and sodium benzoate; 8.0% by weight of a mixed solution containing purified water, cocamidopropyl to betaine and sodium chloride; 3.0% by weight of a mixed solution containing purified water, disodium cocoamphodiacetate, sodium lauryl sulfate, hexylene glycol and sodium chloride; 2.8% by weight of a mixed solution containing purified water and acrylate copolymer; 2.5% by weight of Cocamide DEA; 2.0% by weight of Lauramide DEA; 1.0% by weight of dipropylene glycol; 1.0% by weight of a mixed solution containing purified water, amodimethicone, C12-14 Sec-Pareth-7, propylene glycol and phenoxy ethanol; 0.46% by weight of sodium benzoate; 0.3% by weight of Guar hydroxypropyltrimonium chloride; 0.3% by weight of caprylyl glycol; 0.2% by weight of salicylic acid; 0.2% by weight of Panthenol; 0.2% by weight of Panthenol; 0.1% by weight of a mixed solution containing Maltodextrin and Caramel; 0.1% by weight of Niacinamide; 0.1% by weight of sodium chloride; 0.04% by weight of fragrance; 0.0001% by weight of Cocos Nucifera (Coconut) oil; and 0.0001% by weight of citric acid.

Further, the herbal mixed solution may be configured so as to contain 1.6% by weight of Rehmannia Chinensis root extract; 0.5% by weight of butylene glycol; 0.4% by weight of Mentha Arvensis Extract; 0.3% by weight of 1,2-hexanediol; 0.1% by weight of Acorus Gramineus Root Extract; 0.1% by weight of Biota Orientalis Leaf Extract; 0.1% by weight of Chrysanthemum Zawadskii Extract; 0.1% by weight of Panax Ginseng Root Extract; 0.1% by weight of Glycyrrhiza Galbra (Licorice) Root Extract; 0.1% by weight of Lycinum Chinense Fruit Extract; 0.1% by weight of Morus Alba Bark Extract; 0.1% by weight of Xanthium Strumarium Fruit Extract; and 0.005% by weight of ethyl hexyl glycerin with respect to 10% by weight of the entire mixture.

For reference, the efficacy of herbal extracts in each herbal mixed solution is as follows.

Panax Ginseng has the effect of increasing skin resistance, cell regeneration effect, and nutritional supply effect on the scalp. Green tea contains a large amount of polyphenol catechin, and has pore contraction, antibacterial and bactericidal effects. Also, the extract helps skin cell regeneration as a rich nutritional substance. In particular, the saponin component, which is the main component, maintains protein synthesis, and is recognized to have anti-inflammatory, antibacterial activity. Further, a large amount of saponin and the like maintains healthy hair and scalp by anti-inflammatory and antibacterial action while moisturizing and softening the hair and scalp.

Biota Orientalis Leaf is the leaf of Thuja orientalis L., Thuja occidentalis L., Chamaecyparis pisifera (S. et Z.), and has the effects of hemostasis of the blood and expectoration, and is used for symptoms of hair loss and seborrheic dermatitis.

Morus Alba Bark is a major herbal medicine that eliminates paralysis, purifies blood, and brightens the eyes, but in the present invention, it is added to promote the elasticity function to keep the scalp tight, and to promote the discharge of wastes according to the regeneration of the scalp and the activation of pores, which is considered to be the effect of rutin and kava, which are bioactive substances contained in large amounts.

Acorus gramineus Soland of Acorus Gramineus Root/Stem Extract is known in oriental medicine to brighten the ears and eyes, improve the voice, and warm the body. It is known that the roots and stems of Acorus gramineus Soland have detoxifying and paralytic improving effects on the body, and are particularly effective in treating eczema and skin itchiness on the skin.

Chrysanthemum Zawadskii is particdarly effective in protecting women's diseases, is effective in menstrual irregularities, cold hands and feet, is good for headaches and hair loss, and has a function to prevent hair from turning white and prevent arteriosclerosis.

Xanthium Strumarium Fruit is 1-1.5 m high, and the stems has hair along with the leaves and grow straight. The leaves are separated, divided into 3 broad triangular shapes, and have rough serrations on the edge, hairs on both sides, and 3 veins clearly visible on the back side. Flowers bloom in August-September and are yellow in color and hang on the tip of the main stem and the tip of the branch. There are male and female flowers, Male flowers are round and hang at the tip, and female flowers hang at the bottom, with 2 pistils and 2 thorns. The involucre has hook-shaped thorns, and the fruits are achene, with two wrapped in involucre, It attaches well to other objects, and is an annual herb, and its origin is South Korea. It is distributed in South Korea, China, Japan, etc., inhabits fields and roadsides, and is effective for furuncle, sores, skin diseases, and itching.

Lycinum Chinense Fruit reduces DHT content by enhancing cell immunity, and has physiological activity such as preventing hair loss and hair growth, anti-aging, detoxifying, enhancing cell replication function, strengthening capillaries, antioxidant action, blood cholesterol reduction, and collagen synthesis. In oriental medicine, it is used as a tonic or antipyretic, and has no side effects due to its excellent liver function protection. Further, it has the effect of improving eyesight, preventing adult diseases such as diabetes, improving lung and kidney function, and preventing gray hair from occurring when mixed with perilla oil and aged and then applied to the hair. Additionally, Lycinum Chinense Fruit contains betaine, beaxanthin, carotene, thiamine, vitamins A, B1, B2, C, etc. which are ingredients such as hematopoiesis, cholesterol lowering action, antifat action, blood pressure lowering, hypoglycemic action, growth promotion, anticancer action. The efficacy of Lycinum Chinense Fruit is used for low back pain as chronic hepatitis, cirrhosis, tonic and antipyretic.

Mentha Arvensis (old name: mint leaf extract) is a component obtained by extracting the raw material from the leaves and stems of mint. Mint mainly contains menthol, which gives off a unique fragrance and also contains nutrients such as vitamins, and relieves skin fatigue and gives a refreshing feeling, helps in vital skin management, and gives energy to tired skin due to aging, helping to make the skin alive and maintain skin health.

In addition, the oriental herbal composition according to an errbodiment of the present invention may include, in addition to the herbal ingredients mentioned above, a mixed solution containing sodium lauryl sulfate, purified water, disodium phosphate, and sodium carbonate; a mixed solution containing purified water, TEA-lauryl sulfate, and sodium benzoate; a mixed solution containing purified water, Cocamidopropyl betaine, and sodium chloride; a mixed solution containing purified water, disodium cocoamphodiacetate, sodium lauryl sulfate, hexylene glycol, and sodium chloride; a mixed solution containing purified water and an acrylate copolymer; Cocamide DEA, Lauramide DEA, Dipropylene Glycol; a mixed solution containing purified water, amodimethicone, C12-14 Sec-Pareth-7, propylene glycol, and phenylethanol; sodium benzoate; guarhydroxypropyltrimonium chloride; caprylyl glycol; salicylic acid; panthenol; a mixed solution containing maltodextrin and caramel; niacinamide; sodium chloride; fragrance; coconut palm oil; a mixture of surfactants such as citric acid, solvent, preservative, fragrance, PH control agent, conditioning agent, and the like. These components correspond to known components in the composition preparation process, and thus, detailed descriptions thereof will be omitted.

As described above, the oriental herbal shampoo composition according to an embodiment of the present invention comprises the herbal medicine material extract, and not only has a cleansing effect on the scalp, but also has an anti-inflammatory action and a vitality for non-living hair, a blood circulation promoting effect, a hair growth promoting effect, an antifungal effect, a dandruff and itching prevention effect, and a hair loss prevention effect. In addition, the oriental herbal composition according to an embodiment of the present invention can be used as a hypoallergenic shampoo base used for self-made shampoo.

Further, it is possible to make damaged hair healthy by neutralizing the alkalized hair to a weakly acidic state of pH 4.5 to 5.

Hereinafter, a method for preparing an oriental herbal shampoo composition according to an embodiment of the present invention will be described.

As used herein, the term "extract" refers to a preparation obtained by squeezing an extraction target with an appropriate leachate and evaporating and concentrating the leachate, but is not limited thereto, but it may be an extract obtained by extraction treatment, a diluted or concentrated liquid of the extract, a dried product obtained by drying the extract, and a crude or purified product thereof. The Coicis semen-derived essential oil can be prepared using a general extraction method, separation and purification method known in the art. The extraction method is not limited thereto, but preferably, methods such as boiling water extraction, hot water extraction, cold extraction, reflux cooling extraction, or ultrasonic extraction can be used.

The oriental herbal shampoo composition according to the present invention is prepared through the following preparation method.

1. Mixing Materials

The material in the extract state was quantified, put in a mixer, and stirred for 15 to 30 minutes at a speed of 750 to 850 rpm while maintaining a temperature of 80 to 88° C. and mixed. The above mixing conditions are conditions for uniform stirring without deteriorating the characteristics of the material.

2. Charging and Dispersion

This is a step in which the mixture was separately charged into a dissolution tank and dispersed, and then charged into an emulsification tank and stirred.

3. Filtration and Storage

The mixture of materials that have undergone the cooling and maintenance process may contain particulate foreign substances although the starting material is in the extract state. After filtering foreign substances through a filter, it is stored. The filter may be, for example, a screen of 100 to 200 mesh.

Hereinafter, a method for preparing the oriental herbal shampoo composition according to the present invention will be described in detail. The method comprises the steps of:
a) charging a mixture of purified water, Rehmannia Chinensis root extract, butylene glycol, Mentha Arvensis Extract, 1,2-hexanediol, Acorus Gramineus Root Extract, Biota Orientalis Leaf Extract, Chrysanthemum Zawadskii Extract, Panax Ginseng Root Extract, Glycyrrhiza Galbra (Licorice) Root Extract, Lycinum Chinense Fruit Extract, Morus Alba Bark Extract, Xanthium Strumarium Fruit Extract, ethyl hexyl glycerin, sodium lauryl sulfate, disodium phosphate, sodium carbonate, dipropylene glycol, maltodextrin, Caramel in an oil phase dissolution tank, stirring and warming the mixture;
b) charging a mixture of purified water, TEA-lauryl sulfate, sodium benzoate, cocamidopropyl betaine, sodium chloride, disodium cocoamphodiacetate, sodium lauryl sulfate, hexylene glycol, Cocamide DEA, and Lauramide DEA in an emulsification tank, and stirring the mixture at room temperature;
c) charging salicylic acid in an emulsification tank, stirring and warming the mixture;
d) charging and dispersing a mixed solution of guar hydroxypropyltrimonium chloride in a separate dissolution tank;
e) charging a mixed solution of purified water and guar hydroxypropyltrimonium chloride in a separate dissolution tank, and then charging and stirring the mixed solution in an emulsification tank;
f) charging and dispersing a mixed solution of purified water and acrylate copolymer in a separate dissolution tank;
g) charging and stirring a mixed solution of purified water and acrylate copolymer in an emulsification tank and stirring the mixed solution;
h) charging and stirring a mixed solution of purified water, amodimethicone, C12-14 Sec-Pareth-7, propylene glycol, phenoxy ethanol, sodium benzoate, Dexpanthenol, Maltodextrin, Caramel, Niacinamide, sodium chloride, Cocos Nucifera (Coconut) oil, citric acid and fragrance in an emulsification tank; and
i) checking the state of the emulsification tank, followed by filtration and storage.

Preferably, the filtration is carried out with a screen of 100 mesh,

TABLE 1

List of all components of shampoo composition

| NO | Component name | Raw material content | Component ratio in raw material | Component function |
|---|---|---|---|---|
| 1 | Purified water | 47.8998 | 47.89980 | Solvent |
| 2 | Purified water | 10.000 | 6.3950 | Solvent |
|  | Rehmannia Chinensis root extract |  | 1.6000 | Skin conditioner |
|  | Butylene glycol |  | 0.5000 | Skin conditioner |
|  | Mentha Arvensis Extract |  | 0.4000 | Skin conditioner |
|  | 1,2-Hexanediol |  | 0.3000 | Solvent |
|  | Acorus Calamu Root Extract |  | 0.1000 | Skin conditioner |
|  | Biota Orientalis Leaf Extract |  | 0.1000 | Moisturizer |
|  | Chrysanthemum Zawadskii Extract |  | 0.1000 | Skin conditioner |
|  | Panax Ginseng Root Extract |  | 0.1000 | Skin conditioner |
|  | Glycyrrhiza Galbra (Licorice) Root Extract |  | 0.1000 | Skin conditioner |
|  | Lycinum Chinense Fruit Extract |  | 0.1000 | Anti-oxidant |

TABLE 1-continued

List of all components of shampoo composition

| NO | Component name | Raw material content | Component ratio in raw material | Component function |
|---|---|---|---|---|
| | Moms Alba Bark Extract | | 0.1000 | Skin conditioner |
| | Xanthium Strumarium Fmit Extract | | 0.1000 | Skin conditioner |
| | Ethyl hexyl glycerin | | 0.0050 | Skin conditioner |
| 3 | Sodium lauryl sulfate | 10.000 | 9.7900 | Surfactant |
| | Purified water | | 0.1500 | Solvent |
| | Disodium phosphate | | 0.0400 | Buffer |
| | Sodium carbonate | | 0.0200 | Buffer |
| 4 | Purified water | 10.000 | 6.9700 | Solvent |
| | TEA-lauryl sulfate | | 3.000 | Preservative |
| | sodium benzoate | | 0.0300 | Sterilization preservative |
| 5 | Purified water | 8.000 | 5.2000 | Solvent |
| | Cocamidopropyl betaine | | 2.4000 | Surfactant |
| | sodium chloride | | 0.4000 | Viscosity increasing agent |
| 6 | Purified water | 3.000 | 1.5000 | Solvent |
| | disodium cocoamphodiacetate | | 0.6000 | Surfactant |
| | Sodium lauryl sulfate | | 0.4500 | Surfactant |
| | Hexylene glycol | | 0.3000 | Solvent |
| | Sodium chloride | | 0.1500 | Viscosity increasing agent |
| 7 | Purified water | 2.800 | 1.9320 | Solvent |
| | Acrylate copolymer | | 0.8680 | Film forming agent |
| 8 | Cocamide DEA | 2.500 | 2.5000 | Surfactant |
| 9 | Lauramide DEA | 2.000 | 2.0000 | Surfactant |
| 10 | Dipropyl glycol | 1.000 | 1.0000 | Solvent |
| | Purified water | 1.000 | 0.6502 | Solvent |
| 11 | Amodimethicone | | 0.2300 | Hair conditioner |
| | C12-14 Sec-Pareth-7 | | 0.0900 | Emulsifier |
| | Propylene glycol | | 0.0200 | Moisturizer |
| | Phenoxy ethanol | | 0.0098 | Sterilization preservative |
| 12 | Sodium benzoate | 0.4600 | 0.4600 | Sterilization preservative |
| 13 | Guar hydroxypropyltriimonium chloride | 0.300 | 0.3000 | Sterilization preservative |
| 14 | Caprylyl glycol | 0.300 | 0.3000 | Skin conditioner |
| 15 | Salicylic acid | 0.200 | 0.2000 | Hair conditioner |
| 16 | Panthenol | 0.200 | 0.2000 | Hair conditioner |
| 17 | Maltodextrin | 0.100 | 0.0595 | Absorbent |
| | Caramel | | 0.0405 | Cosmetic colorant |
| 18 | Niacinamide | 0.100 | 0.1000 | Hair conditioner |
| 19 | Sodium chloride | 0.100 | 0.1000 | Viscosity modifier |
| 20 | Fragrance | 0.040 | 0.0400 | Fragrance material |
| 21 | Cocos Nucifera (Coconut) oil | 0.0001 | 0.0001 | Skin conditioner |
| 22 | Citric acid | 0.0001 | 0.0001 | pH adjuster |
| Total | | 100.00 | 100.00 | |

The shampoo stock solution was mixed with the herbal extract mixture of Table 1 to prepare a finished shampoo product, and the herbal extract mixed solution was mixed in an amount of 10.00% by weight with respect to the entire shampoo stock solution.

The oriental herbal exit act is an extract of herbal medicine, and was added as a liquid phase, and is obtained by mixing: Panax Ginseng Root Extract, which moisturizes and softens hair and scalp with a large amount of saponin, and maintains healthy hair and scalp by anti-inflammatory and antibacterial action, and the like, Biota Orientalis Leaf Extract used for hair loss symptoms, seborrheic dermatitis, Morus Alba Bark Extract, which promotes the elasticity function of keeping the scalp tight, the regeneration of the scalp, and the discharge of wastes according to the activation of pores, Acorus Calamu Root Extract, which has a very good effect on eczema or skin itching, Chrysanthemum Zawadskii Extract, which is good for headaches and hair loss, and prevents hair from turning white, Xanthium Strumarium Fruit Extract, which is said to be effective for boils, sore throats, skin diseases, and itching, Glycyrrhiza uralensis Fischer, which calms, protects and nourishes the skin, neutralizes and removes or lowers toxic substances, and harmonizes with all drugs, Lycinum Chinense Fruit Extract, which reduces DHT content by strengthening cellular immunity, prevents hair loss and provides hair growth effects, and Mentha Arvensis extract, which emits a unique fragrance and contains nutrients such as vitamins, relieves skin fatigue and gives a refreshing feeling to help vitalize skin care.

The oriental herbal extract mixture is to determine the properties of the shampoo completed by the present invention. In order to form it, a general method of extracting the essence can be applied. That to is, it is possible to extract the active ingredient by a known method of heating the herbal medicine by charging it in water.

In the above-mentioned herbal medicine materials, each component acts on the scalp and hair and synergizes with each other, thereby exhibiting excellent performance for maintaining a healthy scalp and hair.

The additive is trace amounts of a thickener, an emulsifier, a fragrance, etc., and the ingredients necessary to make up the shampoo are selectively added.

When each oriental shampoo composition of the present invention is prepared as described above, purified water, surfactant, thickener, oil dissolving agent, anti-dandruff agent, moisturizing agent, conditioning agent, emulsifier, etc. are mixed, and then stirred for 3 to 5 minutes at a speed of 400 rpm while heated to a temperature.

After that, similarly to the previous conditions in the state where conditioning agent, refreshing agent, preservative, and fragrance were added, the mixture was sufficiently stirred at a speed of 400 rpm for 3 to 5 minutes in a state of heating to a temperature of about 80 degrees Celsius.

Through the above process, a sticky liquid in the form of a mucus is formed. When it is filtered through a fine mesh and purified to remove solids, the composition of the herbal shampoo composition according to the present invention is completed. The shampoo composition configured as described above is put into a suitable container and packaged so that it can be used as much as necessary for commercialization.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing an oriental herbal shampoo composition, the method comprising the steps of:
 a) charging a mixture of purified water, Rehmannia chinensis root extract, butylene glycol, Mentha arvensis extract, 1,2-hexanediol, Acorus gramineus root extract, Biota orientalis leaf extract, Chrysanthemum zawadskii extract, Panax ginseng root extract, Glycyrrhiza galbra (licorice) root extract, Lycinum chinense fruit extract, Morus alba bark extract, Xanthium strumarium fruit extract, ethyl hexyl glycerin, sodium lauryl sulfate, disodium phosphate, sodium carbonate, dipropylene glycol, maltodextrin, and caramel in an emulsification tank, followed by stirring and warming the mixture;
 b) providing and charging a mixture of purified water, triethanolamine lauryl sulfate, sodium benzoate, cocamidopropyl betaine, sodium chloride, disodium cocoamphodiacetate, sodium lauryl sulfate, hexylene glycol, cocamide diethanolamine (cocamide DEA), and lauramide diethanolamine (lauramide DEA) into the emulsification tank, followed by stirring the mixture at room temperature;
 c) providing and charging salicylic acid in the emulsification tank, followed by stirring and warming the mixture;
 d) providing and charging a mixed solution of purified water and guar hydroxypropyltrimonium chloride in a separate dissolution tank, and then charging and stirring the mixed solution of purified water and guar hydroxypropyltrimonium chloride into the emulsification tank;
 e) charging and dispersing a mixed solution of purified water and acrylate copolymer in a separate dissolution tank, and then charging and stirring the mixed solution of purified water and acrylate copolymer into the emulsification tank, followed by stirring;
 f) charging and stirring a mixed solution of purified water, amodimethicone, C 12-14 sec-pareth-7, propylene glycol, phenoxy ethanol, sodium benzoate, dexpanthenol, maltodextrin, caramel, niacinamide, sodium chloride, Cocos nucifera oil (coconut oil), citric acid and fragrance into the emulsification tank; and
 g) filtering the mixture in the emulsification tank in order to obtain the oriental herbal shampoo composition, and optionally storing the oriental herbal shampoo composition.

2. The method for preparing an oriental herbal shampoo composition according to claim 1, wherein the filtration was carried out with a screen of 100 mesh.

\* \* \* \* \*